(12) United States Patent
Eichner et al.

(10) Patent No.: US 11,963,812 B2
(45) Date of Patent: Apr. 23, 2024

(54) METHOD AND DEVICE FOR PRODUCING A PANORAMIC TOMOGRAPHIC IMAGE OF AN OBJECT TO BE RECORDED

(71) Applicants: SIRONA DENTAL SYSTEMS GMBH, Bensheim (DE); DENTSPLY SIRONA INC., York, PA (US)

(72) Inventors: Stefan Eichner, Heidelberg (DE); Markus Hülsbusch, Bürstadt (DE)

(73) Assignee: DENTSPLY SIRONA INC., York, PA (US)

( * ) Notice: Subject to any disclaimer, the term of this patent is extended or adjusted under 35 U.S.C. 154(b) by 294 days.

(21) Appl. No.: 17/440,358

(22) PCT Filed: Feb. 25, 2020

(86) PCT No.: PCT/EP2020/054886
§ 371 (c)(1),
(2) Date: Sep. 17, 2021

(87) PCT Pub. No.: WO2020/193041
PCT Pub. Date: Oct. 1, 2020

(65) Prior Publication Data
US 2022/0192616 A1    Jun. 23, 2022

(30) Foreign Application Priority Data

Mar. 22, 2019  (EP) .................................... 19164606

(51) Int. Cl.
*A61B 6/00* (2006.01)
*A61B 6/03* (2006.01)
(Continued)

(52) U.S. Cl.
CPC .............. *A61B 6/5258* (2013.01); *A61B 6/03* (2013.01); *A61B 6/461* (2013.01); *A61B 6/51* (2024.01)

(58) Field of Classification Search
CPC ......... A61B 6/5258; A61B 6/03; A61B 6/461; A61B 6/14; A61B 6/467
See application file for complete search history.

(56) References Cited

U.S. PATENT DOCUMENTS

2005/0175142 A1    8/2005  Tang
2006/0029285 A1*   2/2006  Hein ...................... G06T 5/003
                                                382/260
(Continued)

FOREIGN PATENT DOCUMENTS

CN      101178370 A    5/2008
CN      101416072 A    4/2009
(Continued)

OTHER PUBLICATIONS

International Search Report; PCT/EP2020/054886; Apr. 28, 2020 (completed); dated May 13, 2020.
(Continued)

*Primary Examiner* — David P Porta
*Assistant Examiner* — Gisselle M Gutierrez
(74) *Attorney, Agent, or Firm* — DENTSPLY SIRONA INC.

(57) ABSTRACT

The invention relates to a method for producing a panoramic tomographic image (1, 11, 60) of an object (2) to be recorded using a 2D panoramic X-ray device (3), in the course of which X-rays (4) produced by means of an X-ray source (5) irradiate the object (2) and are acquired by means of an X-ray detector (7), wherein, during a movement of the X-ray source (5) and the X-ray detector (7) around the object (2), a number of 2D X-ray projection images (30) are acquired from different acquisition directions (6). A first panoramic tomographic image (1) is calculated from the acquired 2D X-ray projection images (30) using a reconstruction method, wherein the acquired 2D X-ray projection images (30) are modified using a modification method, wherein, from the (Continued)

modified 2D X-ray projection images (40, 50) and using the reconstruction method, a second panoramic tomographic image (11) is calculated with a higher weighting of artifacts (20) relative to anatomical structures (17, 18, 19), wherein a third panoramic tomographic image (60) with significantly reduced artifacts is calculated.

12 Claims, 2 Drawing Sheets

(51) Int. Cl.
*A61B 6/14* (2006.01)
*A61B 6/46* (2024.01)
*A61B 6/51* (2024.01)

(56) References Cited

U.S. PATENT DOCUMENTS

| 2008/0008372 | A1 | 1/2008 | Li |
| 2008/0056549 | A1 | 3/2008 | Hamill |
| 2008/0118022 | A1 | 5/2008 | Hagiwara |
| 2009/0074278 | A1 | 3/2009 | Beaulieu |
| 2017/0011535 | A1 | 1/2017 | Abkai |
| 2017/0273654 | A1* | 9/2017 | Taguchi ............... A61B 6/035 |
| 2021/0407159 | A1* | 12/2021 | Eichner ............... A61B 6/465 |
| 2022/0022827 | A1* | 1/2022 | Maur ................... G06T 7/74 |
| 2022/0202382 | A1* | 6/2022 | Elvers ................. A61B 8/469 |

FOREIGN PATENT DOCUMENTS

| DE | 10016678 | A1 | 10/2001 |
| DE | 102008008733 | A1 | 8/2009 |
| EP | 2975578 | A2 | 1/2016 |
| JP | 2002336239 | A | 11/2002 |
| JP | 2007136163 | A | 6/2007 |
| JP | 2015156966 | A | 9/2015 |
| JP | 2017176268 | A | 10/2017 |
| NL | 1034577 | C1 | 4/2008 |

OTHER PUBLICATIONS

International Preliminary Report on Patentability; PCT/EP2020/054886; Apr. 28, 2020 (completed); dated May 13, 2020.
Written Opinion of the International Searching Authority; PCT/EP2020/054886; Apr. 28, 2020 (completed); dated May 13, 2020.
Chinese Office Action dated Nov. 30, 2023.
Japanese Office Action dated Dec. 26, 2023.

* cited by examiner

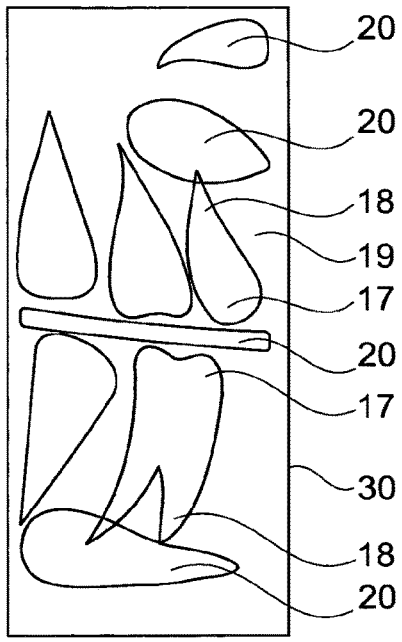
Fig. 2
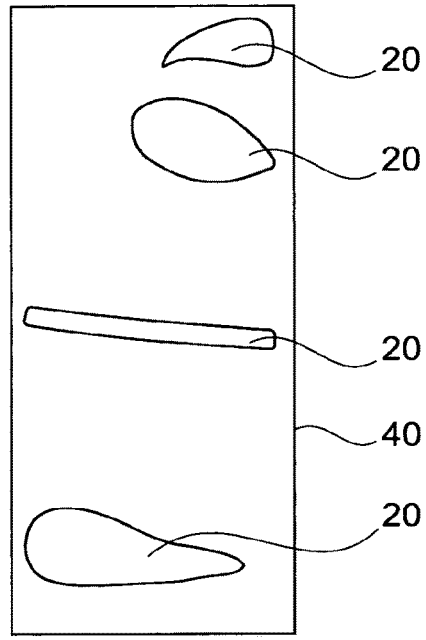
Fig. 3
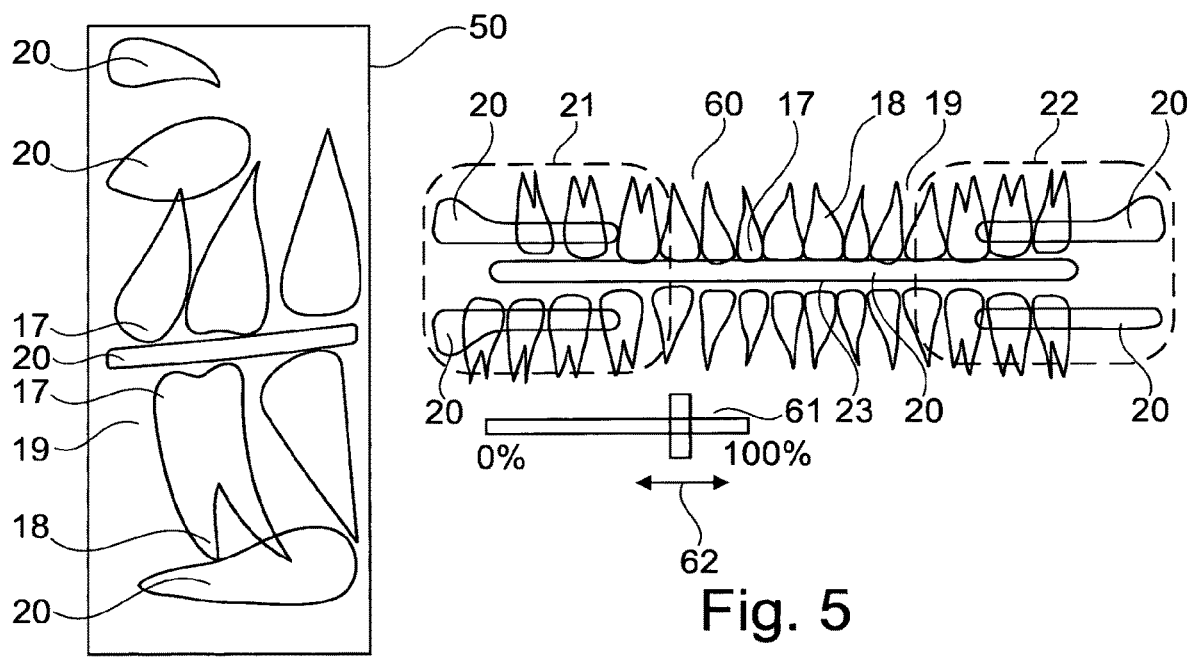
Fig. 4
Fig. 5

METHOD AND DEVICE FOR PRODUCING A PANORAMIC TOMOGRAPHIC IMAGE OF AN OBJECT TO BE RECORDED

TECHNICAL FIELD

The invention relates to a method for producing a panoramic tomographic image of an object to be recorded using a 2D panoramic X-ray device, in the course of which X-rays produced by means of an X-ray source irradiate the object and are acquired by means of an X-ray detector, wherein, during a movement of the X-ray source and the X-ray detector around the object, a number of 2D X-ray projection images are acquired from different acquisition directions.

PRIOR ART

A number of methods for producing panoramic tomographic images are known from the prior art.

DE 102008008733 A1 discloses a method for creating a panoramic tomographic image from a 3D volume, wherein the object to be recorded is virtually irradiated with a virtual X-ray source and the virtually resulting image is acquired with a virtual detector. Unwanted structures in the virtual irradiation can be virtually removed.

DE 10016678 A1 discloses a method for irradiating an object, wherein the object to be examined is irradiated in such a way that interfering objects having high absorption, such as metal fillings, preferably do not interfere with the image of the opposite half of the jaw. In doing so, in particular the beam angle is adjusted to the anatomical structures, i.e. the teeth.

DE 102010040096 A1 discloses a method for creating an image from a 3D volume, wherein a number of virtual projection images are calculated from defined irradiation directions. When calculating the projection images, relevant regions can be weighted more strongly than irrelevant regions. Interfering partial objects, such as fillings or jaw bones, can be cut out of the partial volume or provided with lesser weighting to improve the examination of partial objects, such as teeth, encompassed by the partial volume.

One disadvantage of the mentioned methods is that the artifact correction is performed virtually by cutting out the interfering partial objects or by a slight weighting of said partial objects. For the patient, the radiation exposure for a 3D image is also often greater than for a 2D image. The resolution of a virtual panoramic tomographic image calculated on a 3D volume is lower than that of a classic 2D panoramic tomographic image.

The object of the present invention is therefore to provide a method for producing a 2D panoramic tomographic image that allows an automated and simple reduction of artifacts, for example, opposing jaw artifacts.

PRESENTATION OF THE INVENTION

The invention relates to a method for producing a panoramic tomographic image of an object to be recorded using a 2D panoramic X-ray device. In the course of this, X-rays produced by means of an X-ray source irradiate the object and are acquired by means of an X-ray detector, wherein, during a movement of the X-ray source and the X-ray detector around the object, a number of 2D X-ray projection images are acquired from different acquisition directions. A first panoramic tomographic image is calculated from the acquired 2D X-ray projection images using a reconstruction method. The acquired 2D X-ray projection images are subsequently modified using a modification method, wherein, from the modified 2D X-ray projection images and using the reconstruction method, a second panoramic tomographic image is calculated with a higher weighting of artifacts, for example opposing jaw artifacts, relative to anatomical structures, wherein a third panoramic tomographic image is calculated by combining the first panoramic tomographic image and the second panoramic tomographic image with defined weighting factors such that the artifacts in the third panoramic tomographic image are reduced in comparison to the first panoramic tomographic image.

A panoramic tomographic image is a two-dimensional depiction of the upper jaw and/or the lower jaw of a patient that is acquired using a 2D panoramic X-ray device. The panoramic X-ray device can, for example, comprise an acquisition unit having a digital X-ray detector, wherein, during the acquisition, the digital X-ray detector preferably moves around the face of the patient. The X-ray source synchronously travels around the head, preferably around the back of the head. The X-ray source is designed such that it emits a limited bundle of X-rays which, for example, expands from a width of about 0.25 mm to a width of about 3 mm on the X-ray detector. This bundle penetrates through the jaw sections of the object, whereby the 2D X-ray projection images of the different jaw sections of the entire jaw are acquired individually on the X-ray detector image by image. A panoramic tomographic image is then calculated from the acquired 2D X-ray projection images using a reconstruction method by accordingly merging the individual 2D X-ray projection images together. Merging the individual 2D X-ray projection images produces a tomographic focal layer of the panoramic tomographic image, within which anatomical structures are clearly depicted. This tomographic focal layer generally includes the relevant anatomical structures of the upper jaw and lower jaw, such as teeth, tooth roots and jaw bones. The shape, size and position of the tomographic focal layer are determined by the path of the movement of the X-ray detector relative to the X-ray source in relation to the position of the object, namely the patient head. The anatomical structures of the opposing side of the jaw, which are also located in the beam path, create a shadow and appear blurred within the tomographic focal layer. Such effects are referred to as opposing jaw artifacts, which overlay the objects located within the tomographic focal layer. The position of the tomographic focal layer is therefore determined by the path of the movement of the X-ray detector and the X-ray source relative to the object, wherein the layer thickness of the tomographic focal layer is additionally determined by the width of the irradiated sensor surface of the X-ray detector, i.e. by the width of the respective 2D X-ray projection images, as well as by the movement of the X-ray detector and the X-ray emitter. A narrower width of the X-ray detector leads to an increased layer thickness and a wider X-ray detector leads to a decreased layer thickness within the panoramic tomographic image. A narrower X-ray detector does provide a smaller layer thickness of the tomographic focal layer, but this has the disadvantage that the objects outside the tomographic focal layer superimpose the objects of the tomographic focal layer more strongly.

The digital X-ray detector can be a CCD/CMOS sensor, for example, or a direct conversion sensor having a width of 3 mm to 4 cm. Such an X-ray detector can typically have a physical size with a width of 6 mm and a height of 150 mm. The acquired 2D X-ray projection images can have the same pixel resolution as the used X-ray detector. The pixel size of the acquired 2D X-ray projection images depends on the pixel resolution of the X-ray detector and the binning mode used.

In the course of the movement of the X-ray detector around the object, for example 30 to 1000 2D X-ray projection images can be acquired per second.

In the reconstruction method, the acquired 2D X-ray projection images are summed, for example using a so-called shift and add method, by merging along the acquisition directions, so that the tomographic focal layer within the panoramic tomographic image is formed.

Other known reconstruction methods can also be used to calculate the panoramic tomographic image from the acquired 2D X-ray projection images. One revolution of the movement of the X-ray source and the X-ray detector around the object can, for example, be between 15° and 250°. The 2D X-ray projection images are acquired from the different acquisition directions, for example in angular steps between 0.01° and 10°.

The first panoramic tomographic image is thus calculated from the acquired 2D X-ray projection images as usual by means of the reconstruction method. The acquired 2D X-ray projection images are subsequently modified using the modification method. The modification method can be a low-pass filtering in movement direction, for example, or a horizontal mirroring of the 2D X-ray projection images. By using the modification method, for example a low-pass filtering, the relevant anatomical structures, such as teeth, tooth roots and the jaw bone, are blurry or reduced in the modified 2D X-ray projection images, whereas the interfering image components, such as opposing jaw artifacts, are more dominating. The second panoramic tomographic image is thus calculated from the modified 2D X-ray projection images with a higher weighting of the artifacts relative to the anatomical structures. The artifacts can be opposing jaw artifacts which overlay the actual objects of the tomographic focal layer as a result of the sequence. The artifacts are therefore real structures of the opposing jaw in the beam path of the 2D X-ray projection images.

A third panoramic tomographic image is subsequently calculated by combining the first panoramic tomographic image and the second panoramic tomographic image in such a way that the artifacts, for example opposing jaw artifacts, are reduced in the third panoramic tomographic image.

One advantage of this method is that the reduction of the artifacts is not achieved virtually within a 3D volume by cutting out the interfering partial objects or by a lower weighting of these partial objects, but is instead achieved by modifying the acquired 2D X-ray projection images and calculating a second modified panoramic tomographic image, wherein a third panoramic tomographic image with reduced artifacts is calculated by combining the first panoramic tomographic image with the second modified panoramic tomographic image.

Another advantage of the method is that no novel device is required for carrying out the method. A conventional 2D panoramic X-ray device can be used, whereby the calculation of the second modified panoramic tomographic image and the third panoramic tomographic image takes place in a computer-assisted manner only on the side of the software. The third panoramic tomographic image can advantageously be calculated by subtracting the image information of the second panoramic tomographic image from the image information of the first panoramic tomographic image with defined weighting factors.

In the second modified panoramic tomographic image, regions with artifacts therefore have a higher signal value than the remaining areas so that, by subtracting the image information of the second modified panoramic tomographic image from the original first panoramic tomographic image, a reduction or a complete correction of the artifacts in the third panoramic tomographic image is achieved.

The modification method can advantageously be a low-pass filtering in the movement direction of the 2D X-ray projection images, a local low-pass filtering of the 2D X-ray projection images, and/or a horizontal mirroring of the 2D X-ray projection images.

For a low-pass filtering in movement direction, the individual 2D X-ray projection images are smoothed to the same extent. For low-pass filtering, the same low-pass filter, that is not location-dependent, can be used for each image row of the 2D X-ray projection image.

The second modified panoramic tomographic image, which has a higher relative signal component in the regions of the artifacts in comparison to the other regions of the anatomical structures, is then calculated from the modified 2D X-ray projection images.

Low-pass filtering means a convolution of an image, such as a 2D X-ray projection image, with a low-pass filter kernel (e.g., a Gaussian filter kernel). High-frequency signal components are thereby attenuated relative to low-frequency signal components within the image. Such a filter can be applied in horizontal and/or vertical direction with respect to the overall image or only locally within selected image regions.

Therefore, by using such a low-pass filter, which is globally applied to an image for example, all the pixels of the 2D projection images are more or less attenuated or changed. Image pixels that are very similar (i.e. the same gray value, e.g. in homogeneous image regions) are less modified than image pixels in image regions with fine high-frequency structures or image components.

Locally higher-frequency structures within an image are image regions with fine structures and stronger local gray value changes.

In the 2D projection images, higher-frequency objects are also those structures that change their location within the 2D projection images particularly strongly in terms of time from 2D X-ray projection image to 2D X-ray projection image. In the panoramic tomographic image, those are in particular the anatomical structures that are arranged within the tomographic focal layer and are thus clearly depicted.

Locally low-frequency structures are image regions that have rather weaker or no local gray value changes of structures. Low-frequency structures hardly change between temporally successive 2D X-ray projection images. In the panoramic tomographic image, such low-frequency structures are blurry structures that are not disposed within the tomographic focal layer during the acquisition and thus appear blurred as shadows.

The low-pass filtering can also be location-dependent. With the location-dependent low-pass filtering, only specific regions within the 2D X-ray projection images can be modified to a greater extent. The low-pass filtering can in particular be used within the regions with the high-frequency anatomical structures in order to suppress said structures accordingly.

For the horizontal mirroring, each of the 2D X-ray projection images is mirrored horizontally. The temporally local relationship of high-frequency anatomical structures is thus canceled.

Mirroring an image means rearranging the pixel values in horizontal or vertical direction. For a horizontal mirroring, this means that the last image column is written to the position of the first image column and so on, until the entire image is completely mirrored.

For the reconstruction of the second modified panoramic tomographic image, therefore, only the 2D projection images that have been mirrored and/or filtered with the low-pass filtering are used.

The third panoramic tomographic image can advantageously be displayed using a display device.

The first panoramic tomographic image, the second modified panoramic tomographic image and/or the third panoramic tomographic image can thus be displayed graphically by means of the display device, such as a monitor, so that a user, such as a dentist, can view the panoramic tomographic image for diagnosis.

The weighting factors for the combination of the first panoramic tomographic image with the second panoramic tomographic image can advantageously be managed by means of a virtual tool, so that the strength of the displayed artifacts can be set manually using the virtual tool.

The virtual tool thus allows the weighting between the first panoramic tomographic image and the second panoramic tomographic image to be managed. The virtual tool can be a slider or a rotary controller, for example, or another virtual controller that can be operated manually. The user can thus set a weighting factor between 0% and 100%, for example, whereby, with a weighting factor of 100%, 100% of the second modified panoramic tomographic image is completely subtracted from the first panoramic tomographic image. With a weighting factor of 50%, therefore, the second modified panoramic tomographic image is only subtracted from the first panoramic tomographic image with a weighting of 50%, so that regions with artifacts are still slightly visible.

The virtual tool can advantageously be a slider.

The user can thus easily set the weighting factors with the aid of the virtual slider.

For the combination of the first panoramic tomographic image with the second panoramic tomographic image, the locally varying weighting factors can advantageously be automatically defined adaptively with the aid of a computer as a function of the first and/or the second panoramic tomographic image, wherein regions with artifacts in the second panoramic tomographic image are weighted more strongly than the other regions, so that a stronger reduction of artifacts takes place in these defined regions.

The first and/or the second panoramic tomographic image is thus analyzed in a computer-assisted manner, wherein regions with artifacts, for example opposing jaw artifacts, are defined. These regions with artifacts are then weighted with a locally varying weighting factor, so that these regions with artifacts from the second panoramic tomographic image are subtracted from the first panoramic tomographic image to a greater extent than the remaining areas. The correction of the artifacts thus takes place only in the regions of the panoramic tomographic image in which artifacts appear. In the other regions that primarily include anatomical structures, such as teeth, tooth roots and jaw bones, therefore, only a slight correction or no correction takes place.

An adaptive analysis method for automatically defining the locally varying weighting factors based on the first panoramic tomographic image and/or the second panoramic tomographic image can advantageously use a neural network for machine learning.

A neural network for machine learning is therefore used for the adaptive analysis method.

An artificial neural network for machine learning (CNN) is a computer algorithm that allows the determination of the locally varying weight factors. A method using a CNN is explained in the following.

A convolutional neural network (CNN) is a feed-forward artificial neural network. It is a concept in the field of machine learning that is inspired by biological processes. Convolutional neural networks are used in numerous modern artificial intelligence technologies, primarily in the machine processing of image data.

The structure of a classic CNN generally consists of a convolutional layer followed by a pooling layer. This assembly can in principle be repeated as often as desired. With sufficient repetitions, these are referred to as deep convolutional neural networks, which fall into the field of deep learning. CNNs learn by learning free parameters or classifiers of the convolution kernels layer by layer and learning the weighting thereof when merging with the next layer.

Therefore, with appropriate training data, the neural network learns to identify regions with artifacts in the first and/or second modified panoramic tomographic image automatically. The neural network then learns to weight these selected regions with artifacts more strongly with varying weighting factors, so that the correction of the artifacts only takes place locally in these regions. The neural network can learn using datasets, for example, in which the user has already selected regions with artifacts.

In a further embodiment, for the combination of the first panoramic tomographic image with the second panoramic tomographic image, the locally varying weighting factors can advantageously be automatically defined adaptively with the aid of a computer as a function of a previously known standard model, wherein regions with artifacts within the standard model are defined, wherein said regions in the second panoramic tomographic image are weighted more strongly than the other regions, so that a stronger reduction of artifacts takes place only in these defined regions.

A previously known standard model is thus used to automatically define the regions with artifacts and, based on that, to define the locally varying weighting factors in such a way that the correction of the artifacts takes place only in these defined areas.

The invention further relates to a device for data processing, comprising means for carrying out the abovementioned method.

The device can be a computer, for example, that calculates the first 2D panoramic tomographic image based on the acquired 2D X-ray projection images, modifies the acquired 2D X-ray projection images and, from that, calculates the second modified panoramic tomographic image and the third panoramic tomographic image.

The invention further relates to a computer program, comprising commands which, when the computer program is executed by a computer, cause said computer to carry out the abovementioned method.

The invention further relates to a computer-readable storage medium, comprising commands which, when executed by a computer, cause said computer to carry out the abovementioned method.

BRIEF DESCRIPTION OF THE DRAWINGS

The invention is explained on the basis of the drawings. The drawings show

FIG. 2 a sketch of a 2D X-ray projection image,

FIG. 3 a sketch of a modified 2D X-ray projection image,

FIG. 4 shows a horizontal mirroring of the 2D X-ray projection image of FIG. 2 as a modification method, FIG. 5 shows a graphic depiction of the third

DESIGN EXAMPLES

Figure 1:
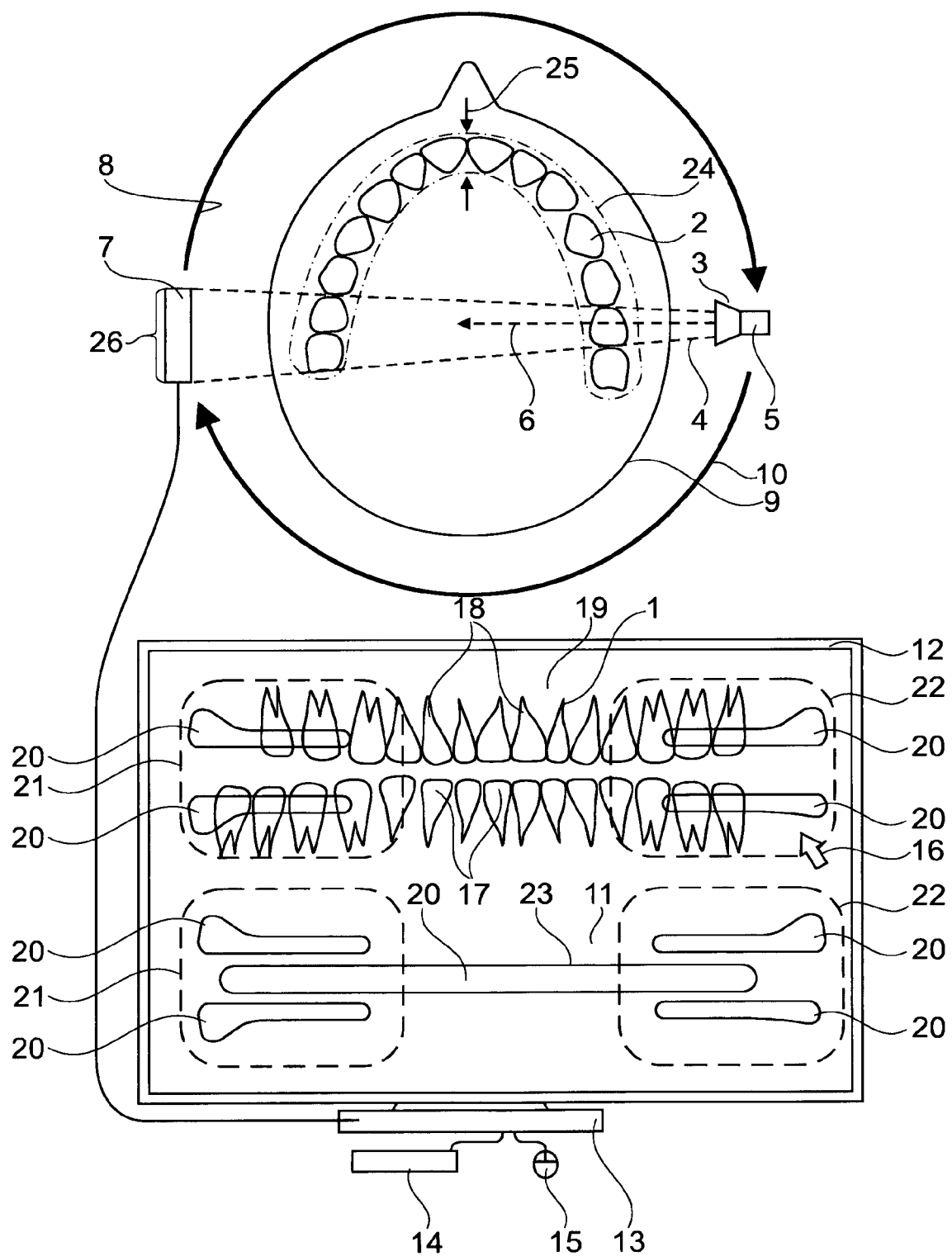
FIG. 1 a sketch for illustrating an embodiment of the present method.

FIG. 1 shows a sketch to illustrate an embodiment of the present method for producing a panoramic tomographic image 1 of an object 2 to be recorded using a 2D panoramic X-ray device 3, wherein X-rays 4 are produced by means of an X-ray source 5 in the form of a limited beam fan, and the object 2, i.e. an upper jaw and/or a lower jaw, is recorded along an acquisition direction 6 using beams and using an X-ray detector 7. During the acquisition, the X-ray detector 7 moves along a movement path 8, for example clockwise, around the object 2 as indicated by the arrow. The X-ray source 5 moves around the back of the head 9 along a movement path 10 as indicated by the arrow. During the continuous movement of the X-ray detector 7 and the X-ray source 5 around the object 2, a number of 2D X-ray projection images are acquired from different acquisition directions 6, for example in angular steps between 0.01° and 10°. Using a reconstruction method, a first panoramic tomographic image 1 is calculated from the acquired 2D X-ray projection images taken from different acquisition directions. The acquired 2D X-ray projection images are subsequently modified using a modification method, wherein a second modified panoramic tomographic image 11 is calculated from the modified 2D X-ray projection images using the reconstruction method. The first panoramic tomographic image and the second modified panoramic tomographic image 11 are graphically displayed by means of a display device 12, such as a monitor. The display device 12 is connected to a computer 13, wherein input means, such as a keyboard 14 and a mouse 15, are connected to the computer 13. A user can navigate within the panoramic tomographic images 1 and 11 with the aid of a cursor 16 using the input means 14 and 15. In the course of one circuit of the movement 8 of the X-ray detector 7 and the synchronous movement 10 of the X-ray source 5, for example 30 to 1000 2D X-ray projection images can be acquired per second. The acquisition direction 6 can be defined as an average irradiation direction, as an average of the individual directions of the X-rays 4 of the beam fan, and varies with respect to the object 2 during acquisition. To calculate a third panoramic tomographic image, the image information of the second modified panoramic tomographic image 11 is subtracted from the image information of the first panoramic tomographic image 1 taking into account the weighting factors. The first panoramic tomographic image 1 includes anatomical structures, such as teeth 17, tooth roots 18 and jaw bones 19, as well as overlaid structures, such as artifacts 20 from the opposing side of the jaw. A first region 21 with increased opposing jaw artifacts 20 on the left end of the first panoramic tomographic image 1 and a second region 22 with the increased opposing jaw artifacts 20 on the right end of the first panoramic tomographic image 1 are indicated with dashed lines. In the second modified panoramic tomographic image 11, the actual anatomical structures 17, 18 and 19 appear blurred as a shadow and thus reduced, whereby the artifacts 20 in the first region 21, in the second region 22 and in a center region 23 have a greater significance in this representation. Therefore, as a result of the modification, the signal component of the artifacts 20 is increased relative to the signal component of the other structures. Subtracting the image information of the second panoramic tomographic image 11 from the first panoramic tomographic image 1 reduces the interfering opposing jaw artifacts in the third panoramic tomographic image. The selection of the regions 21, 22 and 23 with the opposing jaw artifacts 20 can be carried out manually by a user or fully automatically with the aid of a computer using a neural network or a standard model. The neural network can analyze the first panoramic tomographic image 1 and/or the second modified panoramic tomographic image 11 for artifacts 20 and define the corresponding regions 21, 22 and 23. When combining the first panoramic tomographic image 1 with the second panoramic tomographic image 11, locally varying weighting factors can automatically be defined adaptively with the aid of a computer as a function of the defined regions 21, 22 and 23 with the artifacts 20, whereby the image information of the second modified panoramic tomographic image 11 is subtracted from the image information of the first panoramic 1 only in the defined regions 21, 22 and 23, whereby the remaining image information of the first panoramic tomographic image remains unchanged. As a result, therefore, the anatomical structures 17, 18 and 19 are shown more clearly in the calculated third panoramic tomographic image. The user can also define the regions 21, 22, and 23 with the artifacts 20 manually using the cursor 16.

Combining or merging the individual 2D X-ray projection images by means of the reconstruction method produces a tomographic focal layer 24 of the panoramic tomographic image 1, which is indicated with a dash-dotted line and within which the anatomical structures 17, 18, 19 are clearly depicted. The shape, size, position of the tomographic focal layer are determined by the movement of the X-ray detector 7 and the X-ray source 5 relative to the object 2. The anatomical structures 17, 18, 19 that are not located within the tomographic focal layer 24 create a shadow and appear blurred. The position of the tomographic focal layer is therefore determined by the path of the movement of the X-ray detector 5 and the X-ray source 7 relative to the object 2, wherein a width 25 of the tomographic focal layer is also determined by a width 26 of the X-ray detector 7 or by the width of the respective 2D X-ray projection images. A narrower width 26 of the X-ray detector 7 leads to an increasedfocal layer thickness 25 of the tomographic focal layer 24 and a wider X-ray detector leads to a decreased focal layer thickness 25 of the tomographic focal layer 24.

FIG. 2 shows a sketch of a 2D X-ray projection image 30 with anatomical structures, such as the teeth 17, the tooth roots 18 and the jaw bone 19, as well as artifacts 20.

FIG. 3 shows a sketch of a modified 2D X-ray projection image 40, wherein the modification is performed using a low-pass filtering in the movement direction of the 2D X-ray projection image 30. The modification suppresses the higher-frequency anatomical structures 17, 18 and 19, whereby the low-frequency artifacts 20 continue to be depicted clearly with a higher signal proportion compared to the rest of the regions. The first panoramic tomographic image of FIG. 1 is therefore calculated from the acquired 2D X-ray projection images 30 of FIG. 2, whereas the second modified panoramic tomographic image of FIG. 1 is calculated from the modified 2D X-ray projection images 40.

FIG. 4 shows a horizontal mirroring of the 2D X-ray projection image 30 of FIG. 2 as a modification method, whereby a mirrored 2D X-ray projection image 50 is produced. The mirroring removes the local correspondence or relationship of high-frequency anatomical structures of successive 2D X-ray projection images. Calculating the second panoramic tomographic image 11 using the mirrored 2D X-ray projection image 50 allows the anatomical structures 17, 18 and 19 of FIG. 2 to be depicted with a weaker signal component than the artifacts 20 in the second panoramic tomographic image 11. Calculating the mirrored 2D X-ray projection image 50 thus produces a modified 2D X-ray projection image, wherein the second modified panoramic tomographic image 11 of FIG. 1 is calculated from the individual mirrored 2D X-ray projection images using the reconstruction method, in which the anatomical structures are suppressed, but the interfering artifacts 20 are depicted more clearly.

FIG. 5 shows a graphic depiction of the third panoramic tomographic image 60 by means of the display device 12 of FIG. 1, wherein the weighting factors for the combination of the first panoramic tomographic image 1 with the second modified panoramic tomographic image 11 are managed by means of a virtual tool, such as a virtual slider 61. Using the slider 61, the user can adjust the weighting factor of the second modified panoramic tomographic image 11 between 0% and 100% as indicated by the arrow 62. With a weighting factor of 100%, 100% of the image information of the second panoramic tomographic image 11 is subtracted from the first panoramic tomographic image 1, whereas, with a weighting factor of 50%, only 50% of the gray values of the image information from the second panoramic tomographic image 11 is subtracted from the first panoramic tomographic image 1. The adjustment using the slider can also apply to locally varying weighting factors, for example only within the selected regions 21, 22 and 23 with the artifacts 20.

REFERENCE SIGNS

1. First panoramic tomographic image
2. Object
3. 2D panoramic X-ray device
4. X-rays
5. X-ray source
6. Acquisition direction
7. X-ray detector
8. Movement path
9. Back of the head
10. Movement path
11. Second modified panoramic tomographic image
12. Display device
13. Computer
14. Keyboard
15. Mouse
16. Cursor
17. Teeth
18. Tooth roots
19. Jaw bones
20. Artifacts; opposing jaw artifacts
21. First region
22. Second region
23. Center region
24. Tomographic focal layer
25. Focal layer thickness
26. Width of the X-ray detector
30. 2D X-ray projection image
40. Low-pass filtered modified 2D X-ray projection image
50. Mirrored modified 2D X-ray projection image
60. Third panoramic tomographic image with reduced artifacts
61. Slider
62. Arrow

The invention claimed is:

1. Method for producing a panoramic tomographic image of an object to be recorded using a 2D panoramic X-ray device, in the course of which X-rays produced by means of an X-ray source irradiate the object and are acquired by means of an X-ray detector, wherein, during a movement of the X-ray source and the X-ray detector around the object, a number of 2D X-ray projection images are acquired from different acquisition directions, wherein a first panoramic tomographic image is calculated from the acquired 2D X-ray projection images using a reconstruction method, wherein the acquired 2D X-ray projection images are modified using a modification method, wherein, from the modified 2D X-ray projection images and using the reconstruction method, a second panoramic tomographic image is calculated with a higher weighting of artifacts relative to anatomical structures, wherein a third panoramic tomographic image is calculated by combining the first panoramic tomographic image and the second panoramic tomographic image with defined weighting factors such that the artifacts in the third panoramic tomographic image are reduced in comparison to the first panoramic tomographic image.

2. Method according to claim 1, wherein the third panoramic tomographic image is calculated by subtracting the image information of the second panoramic tomographic image from the image information of the first panoramic tomographic image with defined weighting factors.

3. Method according to claim 2, wherein the modification method is a low-pass filtering in the movement direction of the 2D X-ray projection images, a location-dependent low-pass filtering of the 2D X-ray projection images, and/or a horizontal mirroring of the 2D X-ray projection images.

4. Method according to claim 3, wherein the third panoramic tomographic image is displayed by means of a display device.

5. Method according to claim 4, wherein the weighting factors for the combination of the first panoramic tomographic image with the second panoramic tomographic image are managed by means of a virtual tool, so that the strength of the displayed artifacts can be set manually using the virtual tool.

6. Method according to claim 5, wherein the virtual tool is a slider.

7. Method according to claim 4, wherein, for the combination of the first panoramic tomographic image with the second panoramic tomographic image, the locally varying weighting factors are automatically defined adaptively with the aid of a computer as a function of the first panoramic tomographic image and/or the second panoramic tomographic image, wherein regions with artifacts in the second panoramic tomographic image are weighted more strongly than the other regions, so that a stronger reduction of artifacts takes place in these defined regions.

8. Method according to claim 7, wherein an adaptive analysis method for automatically defining the locally varying weighting factors based on the first panoramic tomographic image and/or the second panoramic tomographic image uses a neural network for machine learning.

9. Method according to claim 4, wherein, for the combination of the first panoramic tomographic image with the second panoramic tomographic image, the locally varying weighting factors are automatically defined adaptively with the aid of a computer as a function of a previously known standard model, wherein regions with artifacts within the standard model are defined, wherein said regions in the second panoramic tomographic image are weighted more strongly than the other regions, so that a stronger reduction of artifacts takes place only in these defined regions.

10. Device comprising a computer, a 2D panoramic X-ray device and additional means for carrying out the method according to claim 1.

11. A non-transitory computer-readable storage medium, including instructions that when executed by a computer, cause the computer to:

produce a panoramic tomographic image of an object to be recorded using a 2D panoramic X-ray device, in the course of which X-rays produced by means of an X-ray source irradiate the object and are acquired by means of an X-ray detector, wherein, during a movement of the X-ray source and the X-ray detector around the object, a number of 2D X-ray projection images are acquired from different acquisition directions, wherein a first panoramic tomographic image is calculated from the acquired 2D X-ray projection images using a reconstruction method, wherein the acquired 2D X-ray projection images are modified using a modification method, wherein, from the modified 2D X-ray projection images and using the reconstruction method, a second panoramic tomographic image is calculated with a higher weighting of artifacts relative to anatomical structures, wherein a third panoramic tomographic image is calculated by combining the first panoramic tomographic image and the second panoramic tomographic image with defined weighting factors such that the artifacts in the third panoramic tomographic image are reduced in comparison to the first panoramic tomographic image.

12. A computer system comprising a memory storing instructions that, when executed by the processor, configure the apparatus to:

produce a panoramic tomographic image of an object to be recorded using a 2D panoramic X-ray device, in the course of which X-rays produced by means of an X-ray source irradiate the object and are acquired by means of an X-ray detector, wherein, during a movement of the X-ray source and the X-ray detector around the object, a number of 2D X-ray projection images are acquired from different acquisition directions, wherein a first panoramic tomographic image is calculated from the acquired 2D X-ray projection images using a reconstruction method, wherein the acquired 2D X-ray projection images are modified using a modification method, wherein, from the modified 2D X-ray projection images and using the reconstruction method, a second panoramic tomographic image is calculated with a higher weighting of artifacts relative to anatomical structures, wherein a third panoramic tomographic image is calculated by combining the first panoramic tomographic image and the second panoramic tomographic image with defined weighting factors such that the artifacts in the third panoramic tomographic image are reduced in comparison to the first panoramic tomographic image.

\* \* \* \* \*